(12) United States Patent
Harvie

(10) Patent No.: US 12,102,523 B2
(45) Date of Patent: Oct. 1, 2024

(54) IMPLANT

(71) Applicant: GC Aesthetics (Distribution) Limited

(72) Inventor: Fraser Harvie, Glasgow (GB)

(73) Assignee: GC Aesthetics (Distribution) Limited, Dublin (IE)

( * ) Notice: Subject to any disclaimer, the term of this patent is extended or adjusted under 35 U.S.C. 154(b) by 871 days.

(21) Appl. No.: 17/044,701

(22) PCT Filed: Apr. 3, 2019

(86) PCT No.: PCT/EP2019/058375
§ 371 (c)(1),
(2) Date: Oct. 1, 2020

(87) PCT Pub. No.: WO2019/193035
PCT Pub. Date: Oct. 10, 2019

(65) Prior Publication Data
US 2021/0038367 A1    Feb. 11, 2021

(30) Foreign Application Priority Data

Apr. 4, 2018   (GB) .................................. 1805484

(51) Int. Cl.
*A61F 2/12* (2006.01)
(52) U.S. Cl.
CPC .......... *A61F 2/12* (2013.01); *A61F 2220/005* (2013.01); *A61F 2250/0043* (2013.01)
(58) Field of Classification Search
CPC ................ A61F 2/12; A61F 2220/005; A61F 2250/0043
See application file for complete search history.

(56) References Cited

U.S. PATENT DOCUMENTS

| | | | |
|---|---|---|---|
| 3,356,090 A | 12/1967 | Plantinga et al. | |
| 3,755,042 A | 8/1973 | Robertson et al. | |
| 4,531,244 A | 7/1985 | Hamas | |
| 4,792,336 A | 12/1988 | Hlavacek et al. | |
| 4,795,463 A | 1/1989 | Gerow | |
| 5,500,019 A | 3/1996 | Johnson et al. | |
| 8,808,322 B2 * | 8/2014 | Jones | A61B 90/02 623/8 |

(Continued)

FOREIGN PATENT DOCUMENTS

BR   1320 1201 6489 E2   10/2015
CN   205181341 U  *  4/2016

(Continued)

OTHER PUBLICATIONS

GB Search Report regarding Application No. GB1703631.0, dated Jul. 7, 2017, 3 pages.

(Continued)

*Primary Examiner* — Suzette J Gherbi
(74) *Attorney, Agent, or Firm* — Knobbe, Martens, Olson & Bear LLP

(57) ABSTRACT

An implant comprising a shell, a core within the shell, and a conductive layer between the core and the shell; wherein the implant additionally comprises a sensor for detecting a change in one or more electrical properties of the conductive layer. A kit for use in detection of rupture an implant comprising the implant, a method of detecting rupture and a method of manufacture of an implant.

19 Claims, 5 Drawing Sheets

(56) References Cited

U.S. PATENT DOCUMENTS

| | | | |
|---|---|---|---|
| 9,126,040 B2* | 9/2015 | Zhang | A61N 1/36039 |
| 9,457,133 B2* | 10/2016 | Ruane | A61F 2/28 |
| 10,765,501 B2 | 9/2020 | Van Epps et al. | |
| 10,905,466 B2 | 2/2021 | Chacon Quiros et al. | |
| 11,234,808 B2 | 2/2022 | Govari et al. | |
| 2003/0036803 A1 | 2/2003 | McGhan | |
| 2006/0111777 A1 | 5/2006 | Chen | |
| 2007/0239260 A1* | 10/2007 | Palanker | A61F 2/82 |
| | | | 623/1.15 |
| 2008/0082177 A1 | 4/2008 | Yang | |
| 2009/0012372 A1* | 1/2009 | Burnett | A61B 5/076 |
| | | | 600/300 |
| 2009/0125107 A1 | 5/2009 | Maxwell | |
| 2009/0254179 A1* | 10/2009 | Burnett | A61B 5/14539 |
| | | | 623/8 |
| 2011/0054604 A1 | 3/2011 | Becker | |
| 2011/0082545 A1 | 4/2011 | Freund | |
| 2011/0098576 A1* | 4/2011 | Hollstien | A61B 5/4851 |
| | | | 600/476 |
| 2011/0106249 A1 | 5/2011 | Becker | |
| 2012/0041555 A1 | 2/2012 | Manesis | |
| 2012/0226352 A1 | 9/2012 | Becker | |
| 2015/0057762 A1 | 2/2015 | Harms et al. | |
| 2015/0112434 A1 | 4/2015 | Felix et al. | |
| 2015/0250582 A1 | 9/2015 | Greenhalgh et al. | |
| 2015/0351900 A1 | 12/2015 | Glicksman | |
| 2015/0359637 A1 | 12/2015 | Miquel et al. | |
| 2016/0038269 A1 | 2/2016 | Altman et al. | |
| 2016/0374720 A1 | 12/2016 | Anderson et al. | |
| 2016/0374797 A1 | 12/2016 | Nguyen | |
| 2017/0049549 A1 | 2/2017 | Bayat | |
| 2018/0092726 A1 | 4/2018 | Van Epps et al. | |
| 2018/0110612 A1 | 4/2018 | Schuessler et al. | |
| 2019/0125401 A1 | 5/2019 | Chacon Quiros et al. | |
| 2019/0350697 A1* | 11/2019 | Algawi | A61L 27/18 |
| 2020/0015973 A1 | 1/2020 | Lindsey et al. | |
| 2020/0100885 A1 | 4/2020 | Harvie | |
| 2020/0100892 A1 | 4/2020 | Limem et al. | |
| 2020/0146801 A1 | 5/2020 | Harvie | |
| 2020/0268499 A1 | 8/2020 | Hill et al. | |
| 2020/0375726 A1 | 12/2020 | Limem et al. | |
| 2021/0085443 A1 | 3/2021 | Kocak et al. | |
| 2021/0204976 A1 | 7/2021 | Chacon Quiros et al. | |
| 2022/0054254 A1 | 2/2022 | Gryskiewicz et al. | |

FOREIGN PATENT DOCUMENTS

| | | |
|---|---|---|
| CO | 7350629 | 8/2015 |
| EP | 0370292 | 5/1990 |
| EP | 1852040 | 11/2007 |
| EP | 2921137 | 9/2015 |
| EP | 3 298 962 | 3/2018 |
| WO | WO 2008/055229 | 5/2008 |
| WO | WO 2009/039373 | 3/2009 |
| WO | WO 2012/103611 A1 | 8/2012 |
| WO | WO 2012/177587 | 12/2012 |
| WO | WO 2013/122568 A1 | 8/2013 |
| WO | WO 2015/176014 | 11/2015 |

OTHER PUBLICATIONS

Written Opinion of the International Searching Authority issued in PCT/EP2019/08375 mailed on Jul. 26, 2019.
International Search Report issued in PCT/TP2019/058375 mailed on Jul. 26, 2019.
Search Report issued in application No. GB1805484.1 dated Sep. 20, 2018.
International Search Report and Written Opinion issued in PCT/EP2019/058375 dated Jun. 26, 2019.
"Estudio de copolímeros poli(pdioxanona) / poliglicólico"—2007 (D2 cited in Colombia).

* cited by examiner

IMPLANT

The invention relates to an implant, a method of making an implant, a kit comprising the implant, and uses thereof. In particular, the invention relates to an implant comprising at least one sensor for rupture detection.

Prosthetic implants, particularly soft prosthetic implants, are medical devices that are surgically implanted into the body to replace or augment body tissue. The most common use of such prostheses is breast reconstruction or augmentation. However, they are also used to modify the appearance of soft tissue in, for instance, the buttocks, chin, calf, abdomen or arms.

Rupture is one of the main complications for prosthetic implants, and a major patient concern. Although the manufacture and subsequent quality, safety and performance of breast implants has significantly improved over the years, they are still susceptible to shell rupture, which mainly arises through mechanical trauma (i.e. from handling, impact injury, or when the implant is in transit), damage from surgical instrumentation (i.e. retractors and suture needles), or from implantation itself.

Rupture may cause pain, tenderness, numbness, or a burning sensation. In addition, in many cases, a physical change may occur, such as to the size or shape of the implant, or redness and inflammation of the skin in the region around the implant. Whilst such symptoms are unpleasant, they provide a warning that rupture may have occurred. A potentially larger concern is the so-called "silent rupture", where it is possible for a patient to not have any symptoms. Such ruptures are a particular problem with silicone implants.

If a rupture is suspected, the most common investigative approach is palpation. However, this approach is not particularly accurate in detecting a rupture, even for highly experienced surgeons, meaning a high percentage of ruptures are likely to be missed. Also, physical squeezing of an implant during palpation could potentially exacerbate a rupture. Ultra-sound imaging can be used as a secondary diagnostic approach. This is more accurate than palpation, but a fair proportion of ruptures remain likely to go undetected using this method. The most effective method of detecting rupture of an implant is Magnetic Resonance Imaging (MRI), a method where only a minimal proportion of ruptures would go unnoticed. However, MRI is both costly and time-consuming; therefore, there remains a need for an alternative method, which offers the sensitivity of MRI, at a lower cost.

US 2006/0111777 describes methods and systems for detecting wall breach in inflatable prostheses. This method is reliant on the intrusion of bodily fluid to electrically alter a signalling circuit. However, the reliance on the ingress of bodily fluids to detect rupture is limiting, as it is only possible to detect rupture post-implantation.

US 2009/0012372 also discloses a system and method for sensing rupture of an implant following implantation into the body. Specifically, a sensor is located on the outer surface of the implant shell permitting monitoring of external shell integrity. However, because of their positioning, such sensors may be prone to damage, for instance during implantation by the surgeon.

The invention is intended to overcome or ameliorate at least some aspects of these problems.

Accordingly, in a first aspect of the invention there is provided an implant comprising a shell, a core within the shell, and a conductive layer between the core and the shell; wherein the implant additionally comprises a sensor for detecting a change in one or more electrical properties of the conductive layer.

The implant will often be an implant selected from buttock, breast, chest, calf, abdominal and arm implants. In many cases, the implant is a breast implant.

The presence of the sensor allows for rupture detection. Monitoring of the electrical properties of a conductive layer to determine whether rupture has occurred provides for a single point detection system that is not reliant upon the ingress of bodily fluids nor the egress of core material. A single point detection system is simpler, faster, and more reliable than systems, which require sufficient movement of bodily fluid/core material for detection. Such systems would not detect rupture until significant movement of bodily fluid/core material has occurred. This reliance is limiting, as the speed of ingress/egress of bodily fluid/core material, and the volume of bodily fluid/core material will vary depending on numerous factors, such as the size of the rupture or the activity level of the patient. In contrast, the claimed implant provides a single point detection system, reducing false positive results, whilst improving reliability and sensitivity.

A further advantage of a single point detection system is the ability to measure shell integrity of implants prior to implantation into the body, and also immediately after implantation. Implants can be damaged by handling, and when in transit. However, it may not always be possible to visualise a small rupture with the naked eye. Therefore, it would be beneficial for surgeons to be able to measure the integrity of the implant shell prior to implantation, ensuring that it is safe to proceed by preventing insertion of an already damaged implant.

Also, the physical act of implantation, and exposure to surgical tools can potentially bring about ruptures of the implant shell. Therefore, it would also be beneficial to be able to check shell integrity of the implant immediately after implantation, often prior to bringing the patient around from general aesthesia, so as to highlight whether any damage to the implant has occurred during surgery as a result of excessive manipulation/handling, instrument and/or suture needle trauma. This would potentially remove the need for a secondary operation earlier than anticipated, which would be beneficial to the patient, and save further hospital costs. As it is unlikely that bodily fluids would ingress to a level required to give an accurate reading at such an early stage post-implantation, determination whether an implant has ruptured immediately after surgical implantation would also require a method of detection of rupture that was immediate, and not reliant on the ingress of bodily fluids. Therefore, an implant according to the invention would also be suitable for checking shell integrity of an implant immediately after implantation, overcoming another limitation of current detection systems of the state of the art.

It will generally be the case that the implant core comprises a gel-fill biomaterial, selected from silicone, saline or a combination thereof. As will be understood, the use of biocompatible materials is paramount for implantation of a foreign body into the human body, such as an implantable prostheses.

The conductive layer may be adhered to the innermost layer of the shell, which can also be referred to as the "critical layer." The innermost shell layer can be referred to as the "critical" layer, as it is the layer of shell directly in contact with the core material. Therefore, rupture of this layer means that implant replacement is required, and should be arranged as soon as possible quickly, before potential egress of the core into the body cavity and associated medical problems occurs. Often the conductive layer is adhered to the inner surface of the critical layer and often in direct contact with the gel-fill biomaterial.

Early detection of rupture of the critical layer is advantageous, as it will mean treatment can be sought before the core material can seep into the body cavity. There may be instances where a rupture of the critical layer is so small and the volume and speed of ingress/egress of bodily fluid/core material is subsequently so insignificant, that with conventional methods, detection of rupture may not be possible. Whereas, with the single-point detection system of the invention, which measures a change in one or more electrical properties of the conductive layer, it is possible to detect even minor ruptures. Therefore, having the conductive layer adhered to the innermost layer of the shell allows for the possibility of early detection of even minor ruptures.

Preferably, the conductive layer is a coating on the innermost surface of the layer. Application of a coating would allow for even distribution of the conductive layer on the inner surface, and provide for rapid and simple manufacture of the implant.

The conductive layer may partially cover the innermost surface of the shell. Herein, the term "innermost surface" means the entire innermost surface of the implant shell excluding the injection patch, through which the implant may be filled. The term "partially" means at least 20 to 60% will be covered, and often 40 to 60%.

Preferably, the conductive layer covers substantially all of the innermost surface of the shell. The term "substantially" means in the region of 85% to 100% will be covered, often 90 to 99.5%, and preferably at least 95 to 99.5%.

In the case where the conductive layer partially covers the innermost surface of the shell, it may comprise at least one conductive strip. Where there is a single conductive strip, this may be arranged as a band around the inner surface of the shell, either adhered to this surface, or "floating" between the shell and the core. It will often be the case, however, that to help ensure a greater coverage of the shell, so that ruptures are detected across a wider variety of positions within the implant, there be multiple conductive strips. These may be arranged radially, akin to the lines of longitude on the earth, or in bands, akin to latitudinal lines. They may also be a combination on these, often woven where this is the case. As the skilled person will appreciate, other configurations will also be possible, to provide coverage of the inner surface of the shell with an at least partial conductive layer.

It may also be the case that the conductive layer comprises further conductive strips embedded within the shell (with the exclusion of the external layer), wherein the further conductive strips are radially aligned with the conductive strip of the conductive layer. This configuration would provide for a change in the electrical properties of the conductive layer when an externally originating rupture has yet to reach the critical layer, providing for an early warning of rupture.

Generally, the conductive layer will comprise a conducting material or a combination of conducting materials. When the conductive layer is a coating, the conducting material is generally selected from gold, silver, graphite, or a combination thereof. Gold, silver and graphite are all biocompatible. When the conductive layer comprises at least one conductive strip, the conductive material may be metal leaf selected from gold silver or copper. Silver is advantageous in view of its antimicrobial properties.

It is generally the case that the conducting material (or materials) is nanoparticulate. As used herein, the term "nanoparticulate" is intended to include particles in the range of 1-100 nm, often 10-80 nm, and sometimes 30-50 nm.

An advantage to using nanoparticulate conducting material in the conductive layer is the high surface area to volume ratio, which would result in a more sensitive and efficient conductive layer. Further, as the thickness of the conductive layer is limited by the particle diameter, smaller particulates also provide for thinner conductive layers. This can be particularly advantageous where the conductive layer is a coating. Also, a specific advantage to silver nanoparticles is that their antibacterial efficiency would be enhanced because of the high surface area relative to volume.

The sensor is generally in electrical communication with the conductive layer. It is generally the case that the sensor is positioned between the conductive layer and the core. Often it will be the case that the sensor is connected to the conductive layer, either directly or via a tether. Direct connection of the sensor to the conductive layer provides for as small a communication distance as possible, which would result in a faster, more efficient response. Connection via a tether provides for greater protection of the sensor against impact, as it is positioned closer to the core of the implant.

The internal positioning of the sensor ensures that it is protected by the implant shell. Systems where sensors are located externally would be more susceptible to handling damage and potential damage from exposure to internal body conditions. Also, connection of the sensor to the conductive layer will provide for efficient measurement of any changes in electrical properties characteristic of rupture. Also, it will have no effect on the overall aesthetic properties of the implant, and would be less likely to be felt by the user/physician.

It may also be the case that the sensor is powered by induction charging. Induction charging is a simple and effective charging method, which is non-invasive. It is also possible to power the sensor using radio frequency (RF) charging, resonance charging (i.e. magnetic resonance) and ultrasound charging. Further, it may also be the case that the sensor is powered by electrical energy generated from kinetic energy, body heat or radio waves.

The sensor is configured to detect the electrical properties of the conductive layer. Generally, the electrical property will be either electrical impedance or alternating current across the conductive layer. A measurement of an electrical property is a simple measurement to record, and can be recorded in real time. As such, measurement will be reliable.

In addition, the implant may also comprise a pressure and/or temperature sensor. Provision of a pressure and/or temperature sensor would complement the electrical impedance/alternating current reading, further enhancing the accuracy of the detection device, by allowing correlation of the readings.

With regard to pressure, an intact shell within the body cavity will give a pressure reading in the region of 5 to 10% of a baseline measurement taken prior to insertion. If a rupture were to occur, leakage from the shell would result in a lower pressure reading than that of the base line measurement. Therefore, if the pressure measurement taken was lower than the baseline measurement by around 10% to 15%, this could be indicative of rupture. Typically, if the pressure measurement is below the baseline measurement in the range of 5-10%, and often 8-10%, this is indicative of shell rupture.

As indicated above, rupture can bring about sensitivity, inflammation and pain in the region around the implant, such as in the breast. Inflammation can lead to a localized erythema caused by hyperaemia (increased blood flow), which results in dilation of the blood capillaries and results in a localized increase in temperature. Therefore, temperature measurements taken in excess (where excess is within the region of 5 to 10% rise) of core body temperature (37° C.), may be indicative of rupture. Often the temperature increase is in the region of 5 to 8%, but it is also possible to observe a temperature change of greater than 10%, often 10 to 15%, in such cases, implant replacement must be sought urgently.

The sensor may also comprise a microchip and/or memory. A microchip and/or memory would allow for the storage of product information and also baseline information. As used herein, the term "baseline information" relates to the physical properties of the implant where the shell is intact. A baseline measurement is generally the mean of at least two measurements. It is often the case that the baseline measurement is the mean of two measurements. An example of two measurements which could be taken to provide a baseline reading are the pressure reading prior to incisional closure (implant in breast pocket either sub-glandular or muscular) and just after incisional closure. Provision of baseline information allows for comparative measurement analysis, so as to detect if rupture is likely to have occurred. Upon interrogation of the implant, this would allow for the immediate provision of implant status data including diagnosis, without the need for interpretation by a receiving device, as the microchip within the implant could have determined the existence (or absence) of a rupture. In addition, the provision of memory capability would allow for the recordal of data such that an indication of the time elapsed since the rupture could be offered. In such embodiments, means to power the microchip and//or memory may also be provided in the implant, such as battery power.

In a second aspect of the invention there is provided a kit for use in detection of rupture of an implant comprising an implant of the invention and a receiving device, wherein the receiving device is configured to communicate with the implant.

The receiving device may be hand-held or non-portable, such as a desktop or countertop device. Preferably the receiving device is hand-held. Hand-held devices are portable, so are more easily packaged and transported. Also, they are relatively inexpensive, and easier to position near the implant, providing for a more efficient measurement to be taken. The kit of the invention may be used by medical practitioners, in hospitals, GP surgeries or pharmacies for example, or by the implant recipient at home.

It is generally the case that the receiving device is a passive energy source. Passive energy systems are advantageous, as they only require a small amount of energy and effort to maintain and are cost effective. The passive energy source may optionally be a (Radio Frequency Identification) circuitry, which doesn't contain a battery. It is often the case that the power is supplied by the reader.

Communication of the receiving device with the implant may comprise one or more requests for data sent from the receiving device to the sensor within the implant, the receipt of information from the sensor, requests for confirmation of data (correlation routines) or combinations of these. As noted above, the data may be numerical data to be interpreted by the receiver, or (where the sensor includes a microchip and access to baseline data) the data may be a statement that rupture has (or has not) occurred.

The term "communication" herein means electrical communication. As mentioned previously, the sensor detects a change in one or more electrical properties of the conductive layer of the implant, and receipt of this information via a receiving device will enable the user to determine whether rupture has occurred. The combination of the single point detection system of the implant with a receiving device allows for an accurate and instantaneous measurement recording, providing a simple, efficient and sensitive kit for detection of rupture.

Generally, the communication between the receiving device and the implant is wireless, as this removes the need for wired communication which is more complex than wireless communication before implantation, and requires invasive procedures after implantation of the device. Wireless communication may be by way of RIFD (Radio Frequency Identification) circuitry, and the sensor may be an RFID tag containing a receiver coil. Having wireless communication allows for a non-invasive, simple detection kit. Communication may be by use of radio waves (low and high frequency), magnetic induction, resonance and ultrasound waves.

The conductive layer and/or sensor may be configured to receive power from the receiving device. Often, the receiving device is configured to generate a small alternating current across the conductive layer which is measured by the sensor. An advantage to provision of an alternating current across the conductive layer allows for immediate and accurate rupture detection, as any break in the conductive layer will automatically impede such current, which will be picked up by the sensor and fed back to the receiving device. As mentioned above, measurement of an electrical property is a simple measurement to record, and can be recorded in real time, meaning it is an immediate change that can be measured. It will often be the case that the measurements necessary to detect rupture will occur only when the implant is interrogated by the receiving device, as it is at this point that power is provided to the sensor, allowing for the current to be generated and data gathered. However, as noted above the implant could be provided with a power source, to provide for periodic data gathering ready for transfer to the receiving device upon interrogation.

Data may be displayed on the receiving device or an alternative computer, television or tablet screen. It may be the case that the receiving device is a mobile phone.

Generally, software and baseline data can be stored in either the sensor or the receiving device. Storage within the receiving device is advantageous in case of damage to the implant following impact injury, which may result in damage to the sensor and loss of baseline data, it also allows for a simplified implant design as memory, power and/or a microchip cease to be required. However, the storage of baseline data in the sensor is beneficial should the receiving device be misplaced. Software allows for the programmability and interrogation of the sensor or receiving device. Also, storing baseline data, either in the sensor or receiving device, allows for a direct comparison with the measurement taken in real time, so that the user can immediately determine whether a rupture has taken place, and no further data analysis is required. Specifically, it provides for a situation where the information provided to the user is simply a statement that rupture has, or has not, occurred, simplifying the message provided and removing the need for the user to understand the numerical data (such as the electrical conductivity data) recorded.

The kit of the invention is suitable for use in detection of rupture of an implant post implantation (prior to completion of surgery) and for use in detection of rupture of an implant prior to insertion into the body. As mentioned above, in view of the potential for damage through handling, when in transit, and following surgery, it would be beneficial to be able to measure shell integrity of an implant before surgical implantation, and immediately following implantation, as small ruptures not visible to the naked eye may be present, which would usually go undetected. The kit of the invention provides the user with the ability to measure shell integrity at these stages, ensuring that it is safe for a surgeon to proceed (either with implantation, or completion of surgery).

The kit of the invention is also suitable for use following an impact injury. Should a recipient of an implant sustain an impact injury, for their own peace of mind, it would be advantageous to quickly measure whether rupture occurred as a result of said injury. The kit of the invention is particularly useful if only a mild impact injury is sustained, which does not require hospital resources, as the patient could visit a local GP, or even use the kit from home themselves to determine if a rupture has occurred as a result. Therefore, the kit of the invention effectively provides a low-cost quick implant integrity test system, which can be used to immediately provide reassurance, rather than waiting for the next scheduled MRI appointment.

The FDA usually recommends MRI scans to be performed usually around 3 years post implantation, and bi-annually thereafter. The kit and method of the invention are also suitable for this type of routine monitoring, but as a substitute for MRI would minimise this clinical diagnostic regime, and offer significant savings on hospital costs and resources, as there would effectively be reduced hospital out-patient appointments both for clinical and ultrasound imaging examination as well as MRI's. A reduced need for expensive MRI imaging on an out-patient basis would be particularly beneficial to the healthcare industry, and allow them to offer a less intimidating review service to the implant recipient.

In addition to the above uses, the kit of the invention also offers a continuous warning system throughout the implants life-cycle whilst in-situ for silent rupture, allowing immediate referral for an MRI and therefore by-passing clinical examination and imaging. Moreover, at 10 to 15 years post implantation, rupture rates increase, meaning the kit of the invention can also act as a detection system for late stage rupture.

In a third aspect of the invention there is provided a method of detecting rupture of an implant comprising using the kit of the second aspect of the invention, in the steps of:
  (i) placement of the receiving device within communication distance of the implant;
  (ii) measuring an electrical property of the conductive layer of the implant;
  (iii) transmittal of the measurement to the receiving device.

The method of detecting rupture may also comprise the step of activating a sensor within the implant. Inclusion of an additional step of activating the sensor within the implant means that the sensor can remain in-active until a measurement is required, which removes the need for internal power, and will generally be preferable to the recipient of the implant.

It may be the case that measurement and/or transmittal is by the sensor, more specifically, where present, a microchip, this may be the source of the signal.

The sensor may be configured to detect the electrical properties of the conductive layer. It is often the case that the sensor detects the electrical impedance and/or an alternating current across the conductive layer. When a rupture penetrates the innermost surface of the shell, there is resistance to the current. Therefore, an increase in electrical impedance is indicative of rupture of the implant. Measurement of an electrical property is a simple measurement to record, which can be recorded in real time, meaning it is an immediate change that can be measured, providing a sensitive and rapid method for detection of rupture.

As mentioned previously, baseline data for the implant when the shell is intact can be stored in either memory provided with the sensor or the receiving device. The method of detection of rupture involves the step of comparing the baseline data measurement (for an intact implant shell) with the measurement made in real time, and then the additional step of interpreting the data. Storage of baseline data allows for such a comparison to be made immediately, by the sensor or the receiving device, without the need for human analysis of the results.

In a fourth aspect of the invention there is provided a method of manufacture of the implant claimed, comprising the steps of:
  (i) forming an implant shell;
  (ii) providing a conductive layer;
  (iii) providing a sensor;
  (iv) filling the implant; and
  (v) sealing the implant.

It may be the case that the conductive layer provided is a coating in an inner surface of the shell. Alternatively, provision of the conductive layer may be as one or more conductive strips on an inner surface of the shell. Preferably the conductive layer is provided as a coating. It may be the case that the shell is inverted prior to application of the conductive layer.

It may be that the conductive layer is adhered to the inner surface of the shell by way of an uncured layer of silicon. Specifically, the layer or coating of uncured silicon may be applied (either partially or substantially) to the innermost surface of the shell and allowed to rest for a pre-determined time known as the "de-volatisation period." As used herein the term "devolatisation period" is intended to refer to the period over which the solvent evaporates from the silicone solution. The devolatisation period varies depending on both the shape and size of the implant. This period will typically be in the range of 1 to 10 minutes, preferably in the range of 1.5 to 9 minutes. An increase in the devolatisation period allows the surface of the silicone to thicken and form a skin, and the stickiness of the skin subsequently reduces the run-off speed. Upon completion of the de-volatisation period, the conductive layer can be applied. It is generally the case that a polydimethylsiloxane (PDMS) is used as the uncured silicon layer.

Following provision of the conductive layer, the sensor is incorporated. The sensor may be directly connected to the conductive layer, or connected by means of a tether. Once connected, the implant is filled and sealed, and finished using conventional manufacturing steps (i.e. patch attachment, packaging and sterilization).

There is provided a breast implant comprising a shell, a silicone core within the shell, and a conductive layer comprising a nanoparticulate silver coating substantially covering an innermost surface of the shell; wherein the implant additionally comprises an RFID sensor for detecting a change in the electrical impedance of and/or alternating current across the conductive layer, wherein the conductive layer is directly connected to the sensor. Often, the sensor is powered by induction charging. Often the sensor will also comprise a microchip and/or memory, and often a temperature and/or pressure sensor.

Also provided is a kit for use in wireless detection of rupture an implant comprising: the implant and a hand-held receiving device storing software and baseline data; wherein the receiving device offers a passive energy source and is configured to communicate with the implant, for instance through the receipt of information from a sensor within the implant and/or the powering of the implant.

Further provided is a method of detecting rupture of an implant comprising using the kit in the steps of:
(i) placement of the receiving device within communication distance of the implant;
(ii) activating a sensor within the implant.
(iii) measuring electrical impedance and/or alternating current across of the conductive layer of the implant by the sensor;
(iv) transmittal of the measurement from the sensor to the receiving device;
(v) comparing the measurement to baseline data stored in either the sensor or the receiving device; and
(vi) interpreting the data.
wherein an increase in electrical impedance indicates rupture of the implant.

There is provided a method of manufacture of an implant, comprising the steps of:
(i) forming an implant shell;
(ii) providing a conductive layer as a coating in an inner surface of the shell wherein the conductive layer is adhered to the inner surface of the shell using a layer of a PDMS;
(iii) providing a sensor;
(iv) filling the implant; and
(v) sealing the implant.

Unless otherwise stated, each of the integers described may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

In order that the invention may be more readily understood, it will be described further with reference to the figures and to the specific examples hereinafter.

Figure 1:
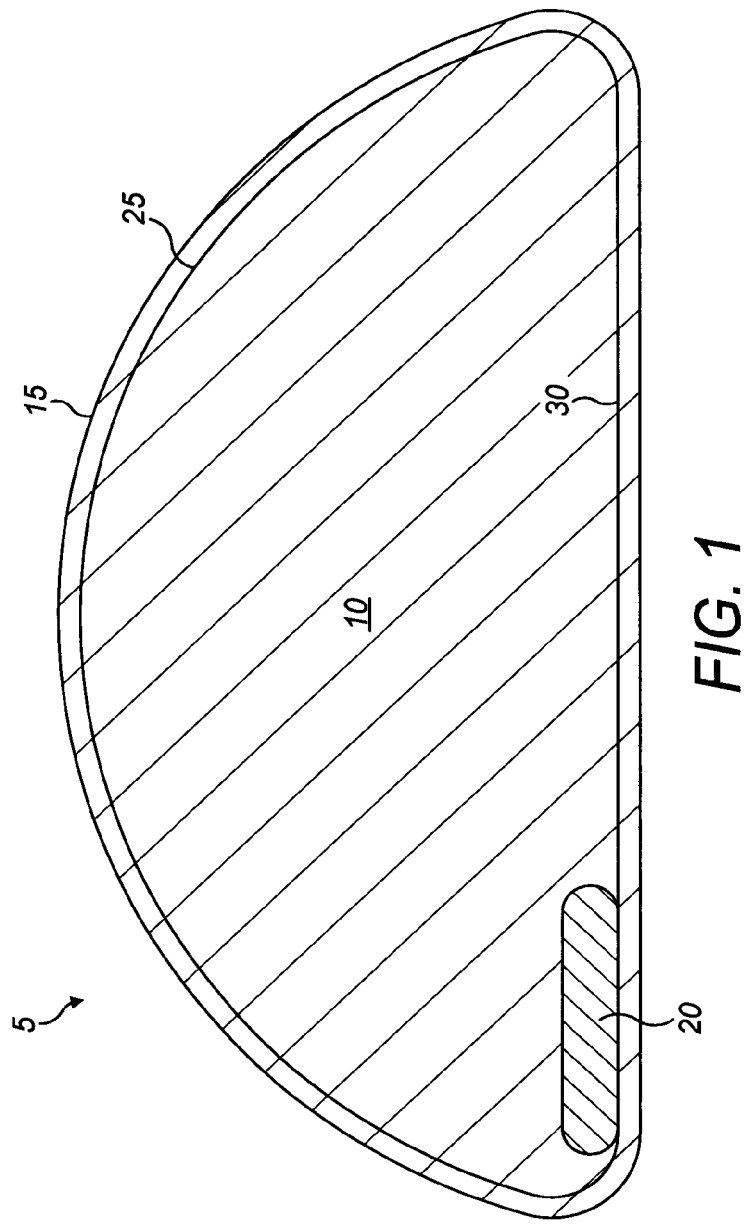
FIG. 1 is a schematic representation of a breast implant of the invention comprising a sensor directly attached to a conductive layer.
Figure 2:
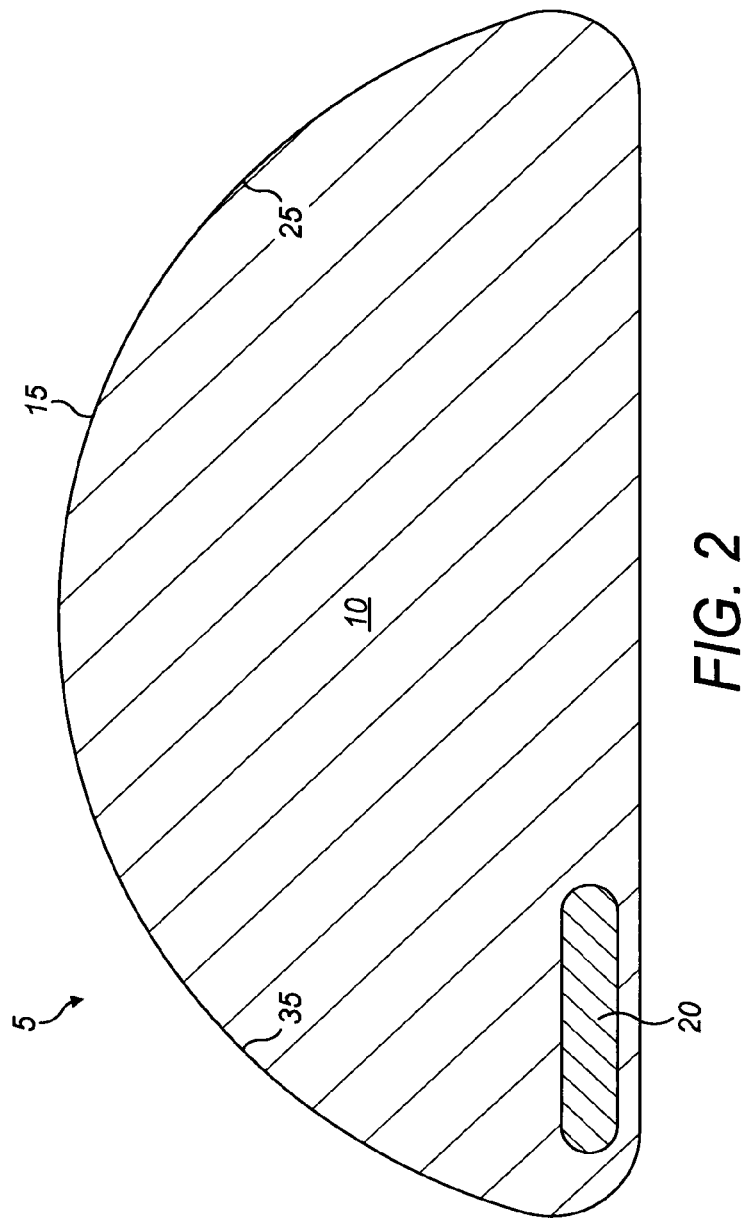
FIG. 2 is a schematic representation of a breast implant comprising a conductive coating.
Figure 3:
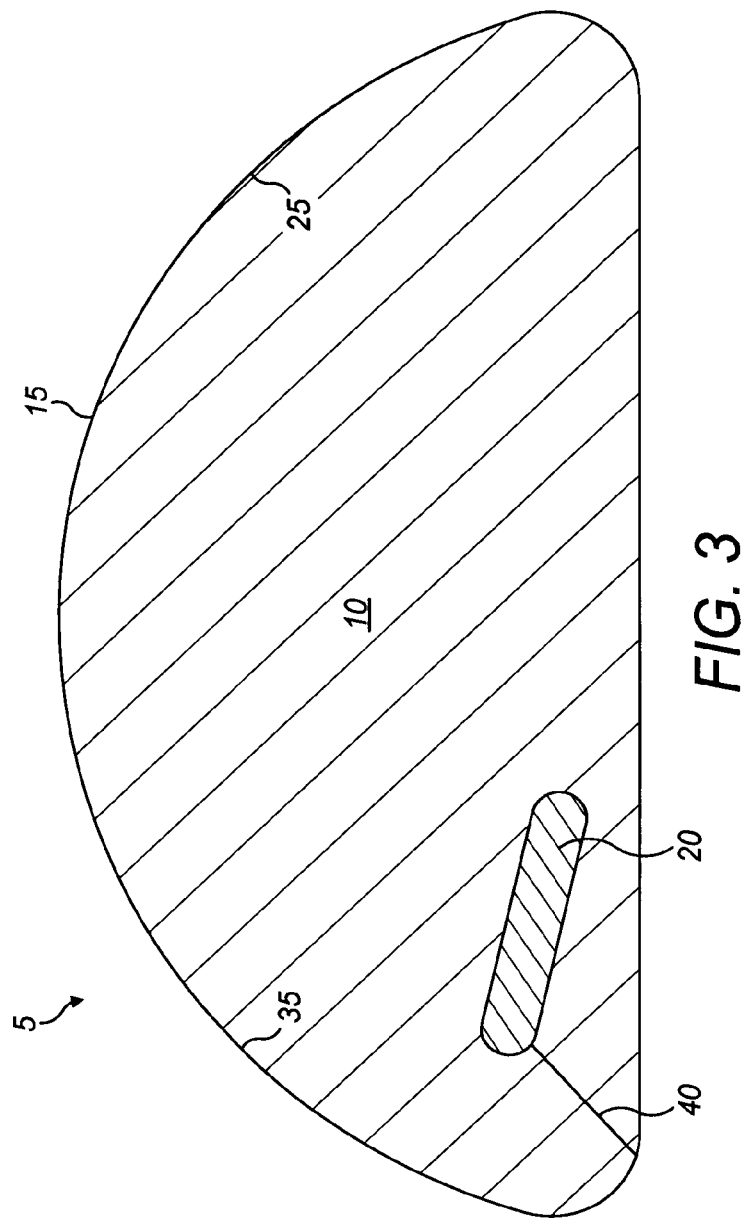
FIG. 3 is a schematic representation of a breast implant comprising a conductive coating and a tethered sensor.

FIGS. 1 to 3 show implant 5 comprising a core 10, a shell 15 and a sensor 20. In addition, a conductive layer 25 is present, between the core 10 and the shell 15. In FIG. 1, the conductive layer 25 is loose between a silicone core 10 and the shell 15, the conductive layer 25 being formed of a silver nanoparticulate film. The sensor 20 is directly attached to the conductive layer 25 on a side of the layer 30 adjacent to the core 10. In FIGS. 2 and 3 the conductive layer 25 comprises a coating on an inner surface 35 of the shell 15. FIG. 3 illustrates the sensor 20 attached to the conductive layer 25 via a tether 40.

Figure 4:
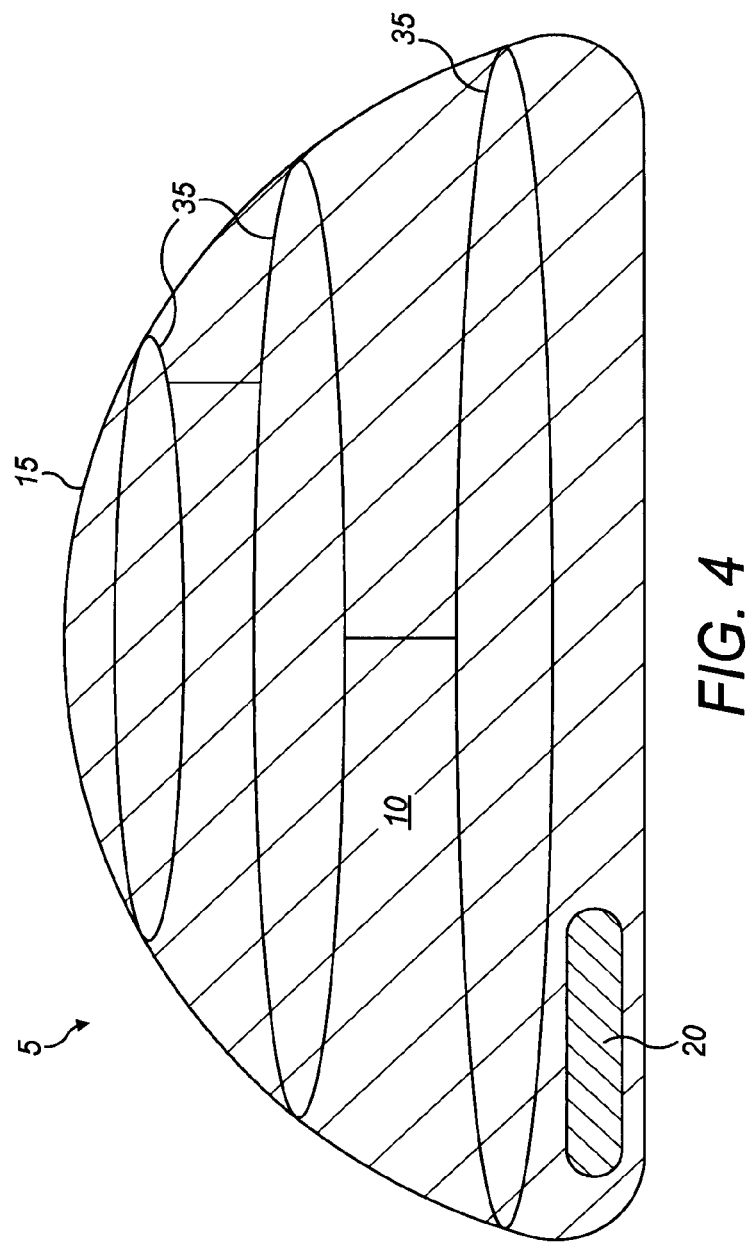
FIG. 4 is schematic representation of a breast implant comprising conducting strips.
Figure 5:
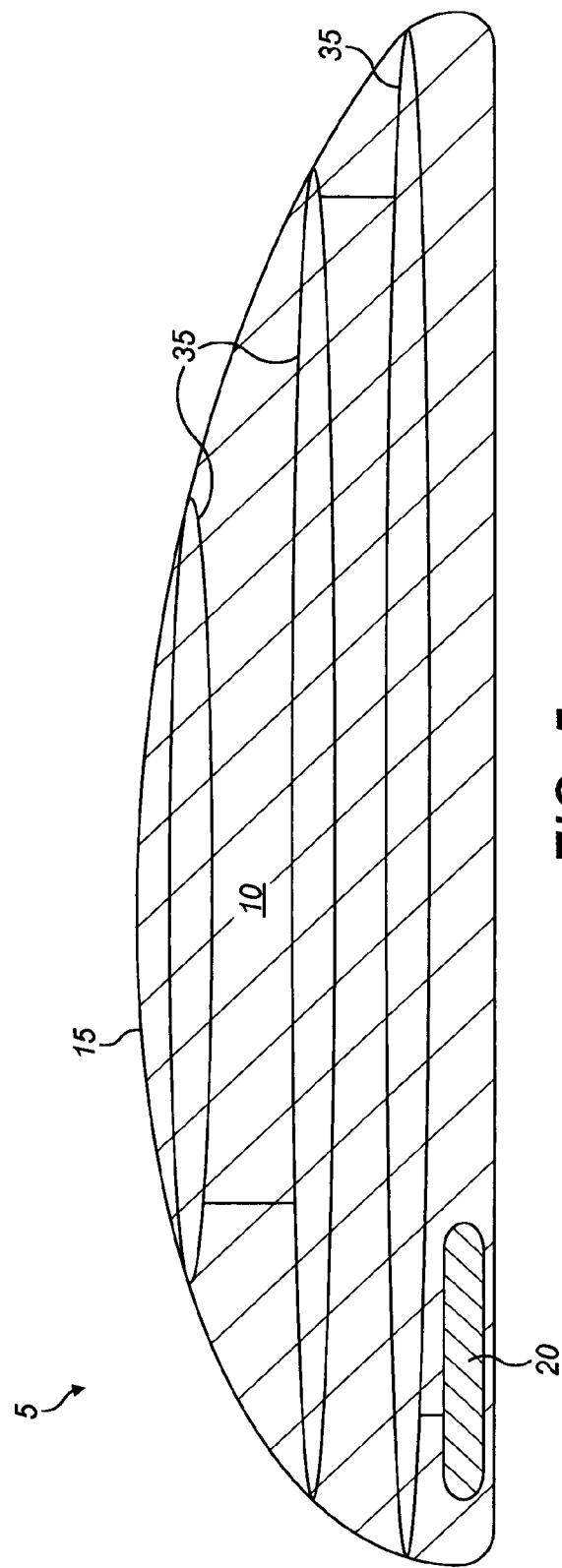
FIG. 5 is a schematic representation of a gluteal implant of the invention comprising conducting strips.

FIGS. 4 and 5 show an implant 5 comprising a core 10, a shell 15 and a sensor 20. In addition, connected circumferential conducting strips 35 attached to the inner shell surface are present between the core 10 and the shell 15. The sensor 20 is directly attached to the inner surface of the shell 15, adjacent to the core 10.

It would be appreciated that the apparatus and methods of the invention are capable of being implemented in a variety of ways, only a few of which have been illustrated and described above.

The invention claimed is:

1. An implant comprising a shell, a core within the shell, and a conductive layer between the core and the shell; wherein the implant additionally comprises a sensor for detecting a change in one or more electrical properties of the conductive layer and wherein the conductive layer is adhered to the shell and comprises a coating on an innermost surface of the shell, and wherein the conductive layer comprises conducting material which is nanoparticulate.

2. An implant according to claim 1, wherein the core comprises a gel-fill biomaterial.

3. An implant according to claim 2, wherein the gel-fill biomaterial is selected from silicone, saline or a combination thereof.

4. An implant according to claim 1, wherein the conductive layer substantially covers the innermost surface of the shell.

5. An implant according to claim 1, wherein the conductive layer partially covers the innermost surface of the shell and wherein the conductive layer comprises at least one conductive strip; and
further comprising conductive strips embedded within the shell, wherein the further conductive strips are radially aligned with the conductive strip of the conductive layer.

6. An implant according to claim 1, wherein the nanoparticulate is selected from gold, silver, copper, graphite or a combination thereof.

7. An implant according to claim 1, wherein the conductive layer is in electrical communication with the sensor.

8. An implant according to claim 7, wherein the conductive layer is connected to the sensor, wherein connection of the sensor to the conductive layer is either direct or via a tether.

9. An implant according to claim 1, wherein the sensor is powered by induction charging.

10. An implant according to claim 1, wherein the electrical property is electrical impedance and/or alternating current across the conductive layer.

11. An implant according to claim 1, wherein the implant further comprises a temperature and/or pressure sensor.

12. A kit for use in detection of rupture an implant comprising:
an implant according to claim 1; and
a receiving device;
wherein the receiving device is configured to communicate with the implant.

13. A kit according to claim 12, wherein the receiving device is hand-held, wherein the conductive layer and/or sensor is configured to receive power from the hand-held receiving device and wherein the receiving device is configured to generate a small alternating current across the conductive layer and/or the sensor.

14. A kit according to claim 12, wherein the receiving device is a passive energy source.

15. A kit according to claim 12, wherein communication of the receiving device with the implant comprises a request for data from the sensor, receipt of information from the sensor within the implant, and optionally requests for correlation of data.

16. A kit according to claim 12, wherein communication of the receiving device with the implant comprises powering of the implant, wherein the conductive layer and/or sensor is configured to receive power from the receiving device.

17. A method of detecting rupture of an implant comprising using the kit of claim 12 in the steps of:
 (i) placement of the receiving device within communication distance of the implant;
 (ii) measuring an electrical property of the conductive layer of the implant; and
 (iii) transmittal of the measurement to the receiving device.

18. A method of manufacture of an implant according to claim 1, comprising the steps of:
 (i) forming an implant shell;
 (ii) providing a conductive layer;
 (iii) providing a sensor;
 (iv) filling the implant; and
 (v) sealing the implant.

19. A method according to claim 18, comprising providing the conductive layer as a coating in an inner surface of the shell wherein the conductive layer is adhered to the inner surface of the shell using a layer of uncured silicone.

* * * * *

UNITED STATES PATENT AND TRADEMARK OFFICE
CERTIFICATE OF CORRECTION

| | | |
|---|---|---|
| PATENT NO. | : 12,102,523 B2 | |
| APPLICATION NO. | : 17/044701 | |
| DATED | : October 1, 2024 | |
| INVENTOR(S) | : Fraser Harvie | |

It is certified that error appears in the above-identified patent and that said Letters Patent is hereby corrected as shown below:

On the Title Page

In item (71) Applicant, Under Column no. 1, Line no. 1, replace "Limited" with "Limited, Dublin (IE)"

Signed and Sealed this
Tenth Day of December, 2024

Katherine Kelly Vidal
*Director of the United States Patent and Trademark Office*